United States Patent [19]

Smirmaul

[11] Patent Number: 4,950,272
[45] Date of Patent: Aug. 21, 1990

[54] SURGICAL INSTRUMENT AND METHOD FOR REMOVING THE LENS OF AN EYE

[76] Inventor: Heinz J. Smirmaul, 1307 Brookstone La., Duncanville, Tex. 75137

[21] Appl. No.: 367,937

[22] Filed: Jun. 19, 1989

[51] Int. Cl.$^5$ .............................................. A61F 9/00
[52] U.S. Cl. .................................................. 606/107
[58] Field of Search ............... 606/107, 110, 161, 166, 606/167, 190

[56] References Cited

U.S. PATENT DOCUMENTS

| | | | |
|---|---|---|---|
| 1,833,687 | 11/1931 | Neivert . | |
| 2,843,128 | 7/1958 | Storz | 128/309 |
| 3,739,784 | 6/1973 | Itoh | 128/320 |
| 3,835,859 | 9/1974 | Roberts et al. | 128/305 |
| 4,436,091 | 3/1984 | Banko | 128/305 |
| 4,538,611 | 9/1985 | Kelman | 128/305 |
| 4,634,187 | 2/1987 | Okada | 128/303.15 |
| 4,693,245 | 9/1987 | Pau | 606/107 |
| 4,706,669 | 11/1987 | Schlegel | 128/329 R |
| 4,732,150 | 3/1988 | Keener, Jr. | 128/320 |
| 4,766,897 | 8/1988 | Smirmaul | 128/305 |
| 4,791,924 | 12/1988 | Kelman | 606/107 |

*Primary Examiner*—Robert A. Hafer
*Assistant Examiner*—Lynda M. Cofsky
*Attorney, Agent, or Firm*—Ross, Howison, Clapp & Korn

[57] ABSTRACT

In accordance with the present invention, an ophthalmic surgical instrument for removing the lens of an eye includes a handle adapted for support in the hand of the user. An elongated tubular member having first and second ends is attached to the handle. The elongated tubular member includes an aperture communicating with the interior of the elongated tubular member and which is disposed between the first and second ends thereof. An arcuate portion of the elongated tubular member extends from the aperture to the second end thereof for receiving the lens. An actuator is mounted to the handle for movement between a forward position and a rearward position with respect to the handle. An elongated rod is disposed within the elongated tubular member and is attached to the actuator, such that movement of the actuator to the forward position causes the rod to extend from the elongated tubular member aperture toward the second end of the elongated tubular member to engage the lens thereby lodging the lens between the second end of the rod and the second end of the elongated tubular member for removal of the lens from the eye. Movement of the actuator to the rearward position causes the rod to retract within the elongated tubular member when not engaging the lens.

5 Claims, 2 Drawing Sheets

SURGICAL INSTRUMENT AND METHOD FOR REMOVING THE LENS OF AN EYE

TECHNICAL FIELD OF THE INVENTION

This invention relates to surgical instruments, and more particularly to an ophthalmic surgical instrument for removing the lens of an eye from the posterior chamber of the eye.

BACKGROUND OF THE INVENTION

The natural lens of an eye is lenticular-shaped body having three portions. The core portion is the nucleus which is surrounded by a cortex. Enclosing the cortex and constituting the wall of the lens is the capsule. The degenerating or degenerated lens of an eye, or a localized point of degeneration within a lens is referred to as a cataract. As a result of a cataractous degeneration, the lens becomes opaque, resulting in visual disability.

Numerous surgical procedures have been developed for removal of cataracted lenses including intracapsular extraction and extracapsular extraction. When the cataract is removed without breaking the capsule, such that the lens is entirely removed, an intracapsular extraction is performed. By contrast, when the forward facing, anterior portion of the capsule is removed followed by separate removal of the lens contents, an extracapsular extraction is performed. Generally, in an extracapsular extraction, the posterior portion of the lens capsule remains in the eye.

In extracapsular cataract extraction, an incision is made into the eye, and the anterior capsule is removed The size of the nucleus dictates the size of the incision which must be made for the cataracted lens to be extracted. An incision of six millimeters to ten millimeters is commonly employed with this technique. During the process of removal of the lens, the lens is moved into the anterior chamber of the eye. The lens may contact the corneal endothelium of the eye resulting in damage of this tissue.

A need has thus arisen for an ophthalmic surgical instrument and method for removing a lens of the eye to thereby minimize any damage to the endothelium layer of the eye In such a procedure, containment of the lens must be accomplished within the posterior chamber prior to removal through the incision made in the eye.

SUMMARY OF THE INVENTION

In accordance with the present invention, an ophthalmic surgical instrument for removing the lens of an eye is provided. The surgical instrument includes a handle adapted for support in the hand of the user. An elongated tubular member having first and second ends is attached to the handle. The elongated tubular member included an aperture communicating with the interior of the elongated tubular member and which is disposed between the first and second ends thereof. An arcuate portion of the elongated tubular member extends from the aperture to the second end thereof for receiving the lens. An actuator is mounted to the handle for movement between a forward position and a rearward position with respect to the handle. An elongated rod is disposed within the elongated tubular member and is attached to the actuator, such that movement of the actuator to the forward position causes the rod to extend from the elongated tubular member aperture toward the second end of the elongated tubular member to engage the lens thereby lodging the lens between the second end of the rod and the second end of the elongated tubular member for removal of the lens from the eye. Movement of the actuator to the rearward position causes the rod to retract within the elongated tubular member when not engaging the lens.

In accordance with another aspect of the present invention, a method for removing a lens of the eye is provided. The method includes inserting into the anterior chamber of the eye a surgical instrument having a handle supported by the user. An elongated tubular member is attached to the handle. The elongated tubular member includes an aperture communicating with the interior of the elongated tubular member and which is disposed between the first and second ends thereof. The elongated tubular member further includes an arcuate portion extending from the aperture to the second end thereof. The instrument further includes an actuator mounted to the handle and a rod disposed within the elongated tubular member which is attached to the actuator. The method includes moving the actuator to a rearward position with respect to the handle, such that the rod is retracted within the elongated tubular member. The arcuate portion of the elongated tubular member is rotated within the posterior chamber of the eye such that the lens is positioned above the arcuate portion and between the elongated tubular member aperture and the second end. The actuator is then moved to the forward position such that the rod is extended from the elongated tubular member aperture to engage the lens and to lodge the lens between the second end of the rod and the second end of the elongated tubular member. The surgical instrument is removed from the eye with the lens lodged therein.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which.

DESCRIPTION OF THE PREFERRED EMBODIMENT

Figure 1:
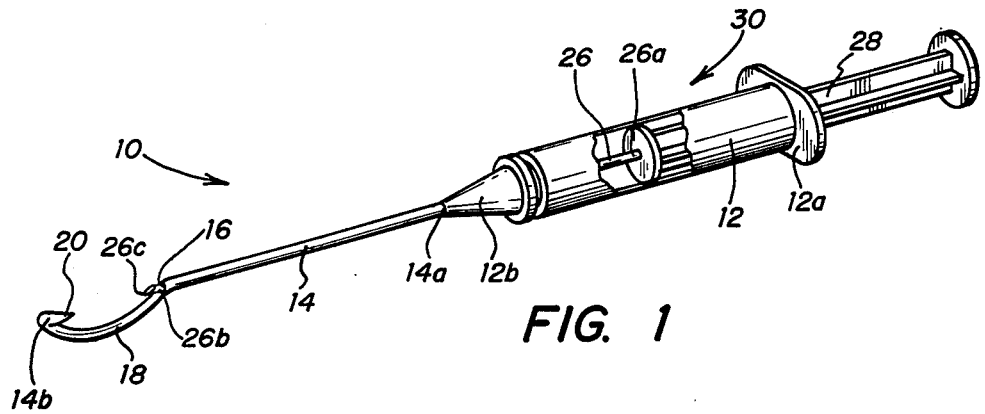
FIG. 1 is a perspective view of the present surgical instrument with the actuator in the retracted position.
Figure 2:
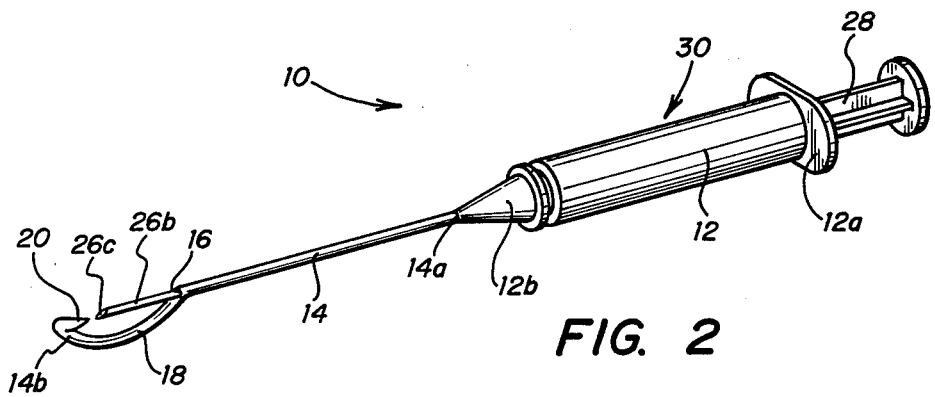
FIG. 2 is a perspective view of the present surgical instrument with the actuator in the extended position.
Figure 3:
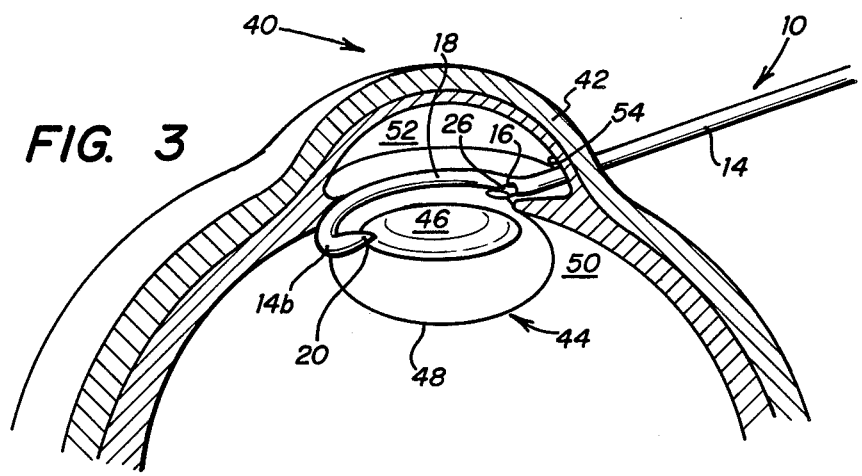
FIG. 3 is a cross-section view of an eye illustrating the present surgical instrument inserted in the anterior chamber with the actuator in the retracted position as shown in FIG. 1.

Referring simultaneously to FIGS. 1 and 2, the present surgical instrument is illustrated and is generally identified by the numeral 10. Surgical instrument 10 includes a handle, generally defined by the numeral 12 having ends 12a and 12b. Handle 12 is adapted to be supported in the hand of a surgeon for use in the surgical procedure of removing a lens from the eye in accordance with the present invention. Surgical instrument 10 may have an overall length of, for example, 10–15 centimeters.

Interconnected to handle 12 is an elongated hollow tubular member, generally identified by the numeral 14. Elongated tubular member 14 includes ends 14a and 14b, and may comprise, for example, a hollow hypodermic needle of, for example, 25 to 20 gauge. End 14a of elongated tubular member 14 is interconnected to end 12b of handle 12.

Disposed between ends 14a and 14b of elongated tubular member 14 is an aperture 16. Elongated tubular member 14 further includes an arcuate portion 18 extending between aperture 16 and end 14b of elongated tubular member 14. End 14b of elongated tubular member 14 terminates in a point 20.

Disposed within elongated tubular member 14 is a stylet or rod 26 having ends 26a and 26b. End 26a of rod 26 is attached to an actuator 28 which is disposed within handle 12. End 26b or rod 26 terminates in a point 26c. Actuator 28 is movable from a rearward position illustrated in FIG. 1, such that rod 26 is completely withdrawn within elongated tubular member 14 to a forward position with respect to handle 12 as illustrated in FIG. 2, such that rod 26 extends through aperture 16 of elongated tubular member 14. Actuator 28 and handle 12 may comprise, for example, a syringe, generally identified by the numeral 30 in which actuator 28 comprises the plunger of syringe 30.

Referring now simultaneously to FIGS. 3–6, the present method of utilizing the present surgical instrument 10 for removing the lens of an eye will be described. FIGS. 3–6 illustrate an eye generally identified by the numeral 40. Eye 40 includes a cornea 42, and a lens generally identified by the numeral 44. Lens 44 includes a lens nucleus 46 disposed within a capsule 48. Lens 44 is generally disposed within the posterior chamber 50 of eye 40 which further includes an anterior chamber 52.

An incision 54 is made through cornea 42 into anterior chamber 52. Surgical instruments to make incision 54 are well-known to those skilled in the art as well as the procedure for making these incisions. The anterior capsule (not shown) of lens 44 is removed from nucleus 46. Surgical instrument 10 is then inserted through incision 54 in the retracted position of actuator 28 as shown in FIG. 1.

Figure 4:
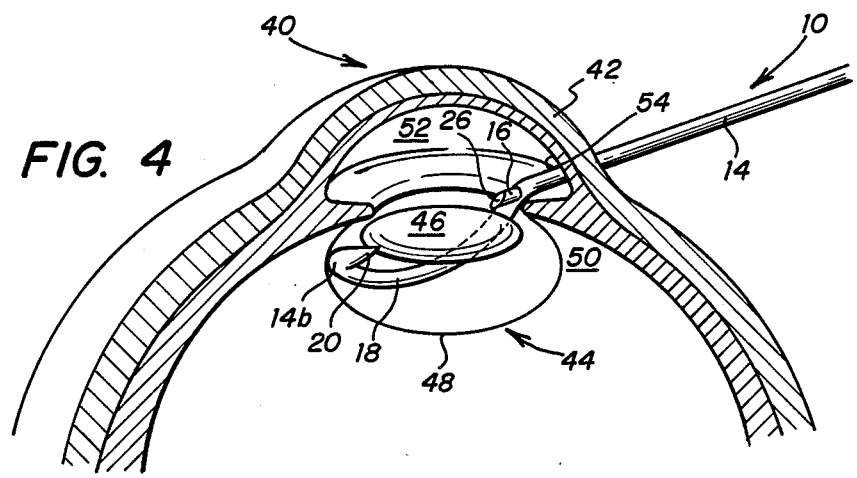
FIG. 4 is a cross-sectional view of an eye illustrating the present surgical instrument with the arcuate portion rotated around the lens positioning the arcuate portion into the posterior chamber.

Referring more specifically to FIG. 4, surgical instrument 10 is rotated into posterior chamber 50 such that arcuate portion 18 is disposed below nucleus 46 and nucleus 46 is disposed between aperture 16 of elongated tubular member 14 and end 14b.

Figure 5:
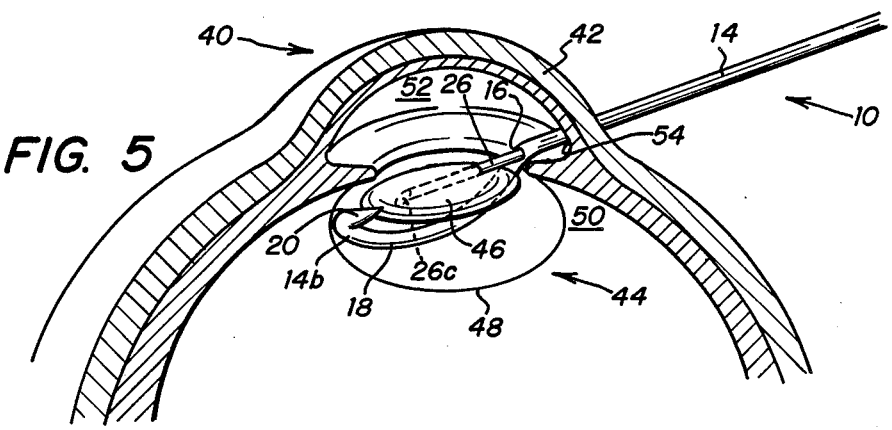
FIG. 5 is a cross-sectional view of an eye illustrating the present surgical instrument with the actuator in the extended position as shown in FIG. 2.

As illustrated in FIG. 5, actuator 28 is then moved to the forward position with respect to handle 12 such that rod 26 extends from aperture 16 of elongated tubular member 14 to thereby engage nucleus 46 and cause nucleus 46 to lodge against point 20 of end 14b of elongated tubular member 14. In this manner, rod 26 causes nucleus 46 to be lodged between rod 26 and end 14b of elongated tubular member 14 such that nucleus 46 is captured and retained by the present surgical instrument 10.

Figure 6:
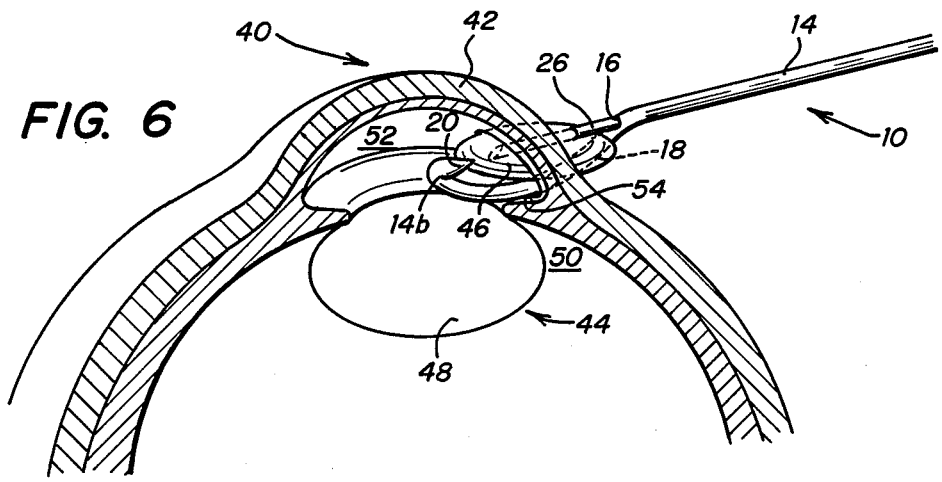
FIG. 6 is a cross-sectional view of an eye illustrating the present surgical instrument having engaged the lens, and the lens partially removed from the eye.

Nucleus 46 can then be removed from posterior chamber 50 with the removal of surgical instrument 10 as illustrated in FIG. 6. Lens nucleus 46 is completely captured and retained by the present surgical instrument 10 during the removal process such that nucleus 46 does not freely move within anterior chamber 52 to damage the endothelium layer of cornea 42.

It therefore can be seen that the present surgical instrument provides for the removal of the nucleus of a lens within the posterior chamber of an eye while preventing the nucleus from contacting the endothelium layer of a cornea.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. An ophthalmic surgical instrument for removing, in substantially one piece, the lens of an eye having an anterior chamber and a posterior chamber, comprising:
   a handle adapted for support in a hand of a user;
   an elongated tubular member having first and second ends, said first end thereof being attached to said handle, said elongated tubular member including an aperture communicating with the interior of said elongated tubular member and being disposed between said first and second ends, said elongated tubular member further including an arcuate portion extending from said aperture to said second end thereof defining an arc of conforming size and shape to the profile of the lens for receiving the entire lens therein and within the posterior chamber of the eye;
   said second end having engaging means for grasping a circumferential portion of the lens;
   actuator means mounted to said handle for movement between a forward position and a rearward position with respect to said handle; and
   an elongated rod disposed within said elongated tubular member and having first and second ends, said first end thereof being attached to said actuator means, such that movement of said actuator means to said forward position causes said rod second end to extend from said elongated tubular member aperture toward said second end of said elongated tubular member to engage in the lens, thereby lodging substantially the entire lens between said rod second end and said second end of said elongated tubular member for fixating the lens within said arcuate portion thereby preventing movement of the lens towards the anterior chamber of the eye and for removing the lens in substantially one piece from the eye, and movement of said actuator means to said rearward position causes said rod to retract within said elongated tubular member when not engaging the lens.

2. The ophthalmic surgical instrument of claim 1 wherein said handle comprises a syringe and said actuator means comprises a syringe plunger.

3. The ophthalmic surgical instrument of claim 1 wherein said second end of said elongated tubular member includes a point for engaging the lens.

4. A method for removing, in substantially one piece, the lens of an eye having an anterior chamber and a posterior chamber, divided by the iris of the eye, the lens being normally disposed in the posterior chamber comprising the steps of:
   inserting into the anterior chamber of the eye a surgical instrument having a handle and an elongated tubular member having first and second ends, the first end thereof being attached to the handle, the elongated tubular member including an aperture communicating with the interior of the elongated tubular member and disposed between the first and second ends thereof, the elongated tubular member further including an arcuate portion extending from the second end thereof and defining an arc of conforming size and shape to the profile of the lens for receiving the lens therein, the instrument further including an actuator mounted to the handle and a rod disposed within the elongated tubular member and having first and second ends, the first end thereof being attached to the actuator;

moving the actuator to a rearward position with respect to the handle, such that the rod is retracted within the elongated tubular member;

rotating the arcuate portion of the elongated tubular member within the posterior chamber of the eye and around the entire lens, such that substantially the entire lens is positioned above the arcuate portion and between the elongated tubular member aperture and the second end thereof;

moving the actuator to a forward position with respect to the handle, such that the rod is extended form the elongated tubular member aperture to engage the lens and thereby lodge the lens between the second end of the rod and the second end of the elongated tubular member thereby fixating the lens within the arcuate portion to prevent movement of the lens towards the anterior chamber of the eye; and removing the surgical instrument from the eye with substantially the entire lens lodged therein.

5. The method of claim 4 wherein the step of moving the actuator to the forward position causes the rod and second end of the elongated tubular member to pierce the lens.

* * * * *